US010624549B2

(12) United States Patent
Shimuta

(10) Patent No.: US 10,624,549 B2
(45) Date of Patent: Apr. 21, 2020

(54) HANDHELD ELECTROCARDIOGRAPHIC MEASUREMENT DEVICE

(71) Applicant: Murata Manufacturing Co., Ltd., Nagaokakyo-shi, Kyoto-fu (JP)

(72) Inventor: Toru Shimuta, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 171 days.

(21) Appl. No.: 15/798,481

(22) Filed: Oct. 31, 2017

(65) Prior Publication Data

US 2018/0064355 A1 Mar. 8, 2018

Related U.S. Application Data

(63) Continuation of application No. PCT/JP2016/062888, filed on Apr. 25, 2016.

(30) Foreign Application Priority Data

May 9, 2015 (JP) ................................. 2015-096115

(51) Int. Cl.
*A61B 5/0404* (2006.01)
*A61B 5/0205* (2006.01)
(Continued)

(52) U.S. Cl.
CPC .......... *A61B 5/0404* (2013.01); *A61B 5/0205* (2013.01); *A61B 5/0408* (2013.01);
(Continued)

(58) Field of Classification Search
CPC . A61B 5/0205; A61B 5/04017; A61B 5/0404; A61B 5/0408; A61B 5/6826
See application file for complete search history.

(56) References Cited

U.S. PATENT DOCUMENTS

| 4,535,783 A | * | 8/1985 | Marangoni | .......... | A61B 5/0404 |
| | | | | | 600/382 |
| 2003/0036685 A1 | * | 2/2003 | Goodman | ............ | A61B 5/0002 |
| | | | | | 600/300 |

(Continued)

FOREIGN PATENT DOCUMENTS

| JP | 2005-000468 A | 1/2005 |
| JP | 5223967 B2 | 6/2013 |

(Continued)

OTHER PUBLICATIONS

Official Communication issued in International Patent Application No. PCT/JP2016/062888, dated Jul. 19, 2016.

*Primary Examiner* — Christopher A Flory
(74) *Attorney, Agent, or Firm* — Keating & Bennett, LLP

(57) ABSTRACT

A handheld electrocardiographic measurement device includes a substantially spheroidal body, a stopper projecting along an axial direction of the body to restrict a position of a thumb of one hand by abutting on a side surface of the thumb when a user grips the body with the one hand, a plate-shaped flange projecting from a side surface of the body in a direction orthogonal or substantially orthogonal to a projecting direction of the stopper, a first electrocardiographic electrode disposed on a back side of the body to touch a finger of the one hand when the body is gripped with the one hand, and a second electrocardiographic electrode disposed on a surface of the flange to touch a finger of the other hand when the flange is pinched by the other hand.

20 Claims, 5 Drawing Sheets

(51) Int. Cl.
*A61B 5/04* (2006.01)
*A61B 5/0408* (2006.01)
*A61B 5/00* (2006.01)
*A61B 5/024* (2006.01)

(52) U.S. Cl.
CPC ........ *A61B 5/04017* (2013.01); *A61B 5/6826* (2013.01); *A61B 5/02427* (2013.01)

(56) References Cited

U.S. PATENT DOCUMENTS

| | | | | |
|---|---|---|---|---|
| 2003/0097078 | A1* | 5/2003 | Maeda | A61B 5/044 600/509 |
| 2004/0260190 | A1* | 12/2004 | Tanabe | A61B 5/0404 600/509 |
| 2005/0004487 | A1 | 1/2005 | Ishida et al. | |
| 2005/0027203 | A1* | 2/2005 | Umeda | A61B 5/0404 600/509 |
| 2008/0238695 | A1* | 10/2008 | Yanai | A61B 5/02427 340/576 |
| 2008/0293491 | A1* | 11/2008 | Wu | A63F 13/06 463/37 |
| 2008/0306395 | A1* | 12/2008 | Xu | A61B 5/02416 600/509 |
| 2009/0015558 | A1* | 1/2009 | Hung | A61B 5/02433 345/163 |
| 2009/0227852 | A1* | 9/2009 | Glaser | A42B 3/0433 600/324 |
| 2009/0299206 | A1* | 12/2009 | Wang | A61B 5/0404 600/522 |
| 2009/0306488 | A1* | 12/2009 | Al-Ali | A61B 5/14551 600/324 |
| 2010/0234745 | A1* | 9/2010 | Umeda | A61B 5/0404 600/509 |
| 2011/0105928 | A1* | 5/2011 | Bojovic | A61B 5/0006 600/515 |
| 2012/0022385 | A1* | 1/2012 | Shimuta | A61B 5/0404 600/509 |
| 2012/0071734 | A1* | 3/2012 | Shimuta | A61B 5/0205 600/301 |
| 2013/0109946 | A1* | 5/2013 | Shim | A61B 5/0006 600/386 |
| 2013/0171599 | A1* | 7/2013 | Bleich | A61B 5/0456 434/247 |
| 2013/0261414 | A1 | 10/2013 | Tal et al. | |
| 2013/0281868 | A1 | 10/2013 | Kawachi et al. | |
| 2013/0310659 | A1* | 11/2013 | Kawachi | A61B 5/0404 600/301 |
| 2014/0088396 | A1* | 3/2014 | Shimuta | A61B 5/0245 600/382 |
| 2014/0163349 | A1* | 6/2014 | Amitai | G16H 40/67 600/393 |
| 2014/0249438 | A1 | 9/2014 | Morikawa et al. | |
| 2015/0073285 | A1* | 3/2015 | Albert | A61B 5/0408 600/509 |
| 2015/0201876 | A1* | 7/2015 | Zhou | A61B 5/0404 600/324 |
| 2017/0055911 | A1* | 3/2017 | Wijayaratna | G16H 10/60 |
| 2017/0340228 | A1* | 11/2017 | Dirkes | A61B 5/746 |
| 2019/0307400 | A1* | 10/2019 | Zhao | A61B 5/02055 |

FOREIGN PATENT DOCUMENTS

| | | |
|---|---|---|
| JP | 2013-226189 A | 11/2013 |
| WO | 2014/038213 A1 | 3/2014 |

* cited by examiner

HANDHELD ELECTROCARDIOGRAPHIC MEASUREMENT DEVICE

CROSS REFERENCE TO RELATED APPLICATIONS

This application claims the benefit of priority to Japanese Patent Application No. 2015-096115 filed on May 9, 2015 and is a Continuation Application of PCT Application No. PCT/JP2016/062888 filed on Apr. 25, 2016. The entire contents of each application are hereby incorporated herein by reference.

BACKGROUND OF THE INVENTION

1. Field of the Invention

The present invention relates to a handheld electrocardiographic measurement device that acquires an electrocardiographic signal.

2. Description of the Related Art

In recent years, public interest in management, maintenance, and promotion of health has been growing. There is a demand that people can more easily obtain biological information, such as a pulse and an electrocardiographic information, in daily life. Japanese Unexamined Patent Application Publication No. 2013-226189 and Japanese Patent No. 5223967 each disclose an electrocardiographic measurement device to be held with both hands to acquire an electrocardiographic signal from palms or fingers of the hands.

More specifically, the device of Japanese Unexamined Patent Application Publication No. 2013-226189 includes a case having a peripheral surface to be held with both hands, and electrocardiographic electrodes for detecting an electrocardiographic signal through the hands holding the case. In particular, the case in this device is spherical, and a left-hand electrode and a right-hand electrode serving as electrocardiographic electrodes are provided in correspondence to the palms or fingers of both hands holding the case.

The electrocardiographic signal detection device of Japanese Patent No. 5223967 is a portable device, and detects an electrocardiographic signal from thumbs of both hands gripping the device. In more detail, the electrocardiographic signal detection device includes a housing made of an insulating material, such as resin. A display window is attached at an opening in an upper surface of the housing. Inside the display window, two electrodes are disposed to detect an electrocardiographic signal. The electrodes are disposed at positions such that the thumbs of both hands can easily touch the electrodes in a state in which the electrocardiographic signal detection device is gripped with the hands. That is, one of the electrodes is disposed on a left proximal side of an upper surface of the display window, and the other electrode is disposed on a right proximal side of the upper surface of the display window.

As described above, in the device of Japanese Unexamined Patent Application Publication No. 2013-226189, when the spherical case is held with both hands, the palms or fingers of the hands come into contact with the electrocardiographic electrodes (left-hand electrode and right-hand electrode), and this allows acquisition of an electrocardiographic signal. However, since this device is held with both hands from the left and right sides, for example, in a situation in which the device cannot be placed on a desk, when electrocardiographic measurement is continued for a long period (for example, about serval minutes), the hands holding the device get tired, and strain is applied to the hands and shoulders. As a result, there is a fear that myoelectric noise will be easily included in the electrocardiographic signal.

In contrast, the electrocardiographic signal detection device of Japanese Patent No. 5223967 is a portable device and can be reduced in size. However, both hands may touch each other during measurement. In this case, if both hands touch each other, the S/N ratio of the electrocardiographic signal may be decreased. However, if the touch of both hands is avoided, it may be difficult to grip the device. Moreover, since the electrocardiographic signal detection device is held while being clamped (pinched) by, for example, thumbs and forefingers, strain is easily applied to the hands, and myoelectric noise is easily included.

SUMMARY OF THE INVENTION

Preferred embodiments of the present invention provide handheld electrocardiographic measurement devices that acquire an electrocardiographic signal from fingers of both hands. In the handheld electrocardiographic measurement devices, the fingers of both hands do not touch each other even when the size is reduced, and rarely become tired even when holding the devices for a long period. This allows the electrocardiographic signal to be stably measured for a long period.

A handheld electrocardiographic measurement device according to a preferred embodiment of the present invention includes a substantially spheroidal body, a stopper projecting along an axial direction of the body to restrict a position of a thumb of one hand by abutting on a side surface of the thumb when a user grips the body with the one hand, a plate-shaped flange projecting from a side surface of the body in a direction orthogonal or substantially orthogonal to a projecting direction of the stopper, a first electrocardiographic electrode disposed on a back side of the body to touch a finger of the one hand when the body is gripped with the one hand, and a second electrocardiographic electrode disposed on a surface of the flange to touch a finger of the other hand when the flange is pinched with the other hand.

With a handheld electrocardiographic measurement device according to a preferred embodiment of the present invention, when the device is held with both hands, one hand (a thumb and the other four fingers) grips the substantially spheroidal body and the fingers of the other hand (for example, a thumb and a forefinger) pinch (clamp) the plate-shaped flange. Since both hands support each other, they rarely get tired even when maintaining their posture for a long period (for example, several minutes). At this time, the finger of one hand (for example, a forefinger and/or a middle finger) touches the first electrocardiographic electrode disposed on the back side of the body, and the finger of the other hand (for example, the thumb and/or the forefinger) touches the second electrocardiographic electrode disposed on the surface of the flange. Since the position of the thumb of the one hand is restricted by the stopper projecting along the axial direction of the body and the plate-shaped flange projects from the side surface of the body in the direction orthogonal or substantially orthogonal to the projecting direction of the stopper, the fingers of both hands are prevented from touching each other. That is, both hands are able to hold the device without touching each other. As a result, even when the size is reduced, the fingers of both hands do not touch each other, and the hands rarely get tired even when holding the device for a long period. This allows an electrocardiographic signal to be stably measured for a long period.

A handheld electrocardiographic measurement device according to a preferred embodiment of the present invention includes a substantially spheroidal body, a stopper projecting along an axial direction of the body to restrict a position of a thumb of one hand by abutting on a side surface of the thumb when a user grips the body with the one hand, a plate-shaped flange projecting from a side surface of the body in a direction orthogonal or substantially orthogonal to a projecting direction of the stopper, a first electrocardiographic electrode disposed at a position offset from the stopper along a circumferential direction of the body to touch a tip of the thumb restricted by the stopper when the body is gripped with the one hand, and a second electrocardiographic electrode disposed on a surface of the flange to touch a finger of the other hand when the flange is pinched with the other hand.

With a handheld electrocardiographic measurement device according to a preferred embodiment of the present invention, when the device is held with both hands, the substantially spheroidal body is gripped with one hand (the thumb and the other four fingers) and the plate-shaped flange is pinched (clamped) with the fingers (for example, the thumb and the forefinger) of the other hand. Since both hands support each other, they rarely get tired even when maintaining their posture for a long period (for example, several minutes). At this time, since the body is gripped so that the thumb of one hand touches the first electrocardiographic electrode disposed in the body and the finger (for example, the thumb and/or the forefinger) of the other hand touches the second electrocardiographic electrode disposed on the surface of the flange, the fingers of both hands are placed close to each other. However, since the position of the thumb of the one hand is restricted by the stopper projecting along the axial direction of the body and the plate-shaped flange projects on the side surface of the body in the direction orthogonal or substantially orthogonal to the projecting direction of the stopper, the fingers of both hands are prevented from touching each other. That is, the device is able to be held while both hands do not touch each other. As a result, even when the size is reduced, the fingers of both hands do not touch each other, and the hands rarely get tired even when holding the device for a long period. This allows an electrocardiographic signal to be stably measured for a long period. Particularly, in this case, since the pair of electrocardiographic electrodes are disposed on the same side (front side), it is possible to easily and visually check whether or not the fingers of both hands are respectively in contact with the corresponding electrocardiographic electrodes.

In a handheld electrocardiographic measurement device according to a preferred embodiment of the present invention, a region of the body where the first electrocardiographic electrode is disposed is preferably lower than a surrounding surface.

In this case, the tip of the thumb is able to be reliably brought into contact with the first electrocardiographic electrode by putting the ball of the thumb in the recess.

In a handheld electrocardiographic measurement device according to a preferred embodiment of the present invention, a stepped portion is preferably provided at a position near a distal end portion of the body on the back side, when viewed from the stopper.

In this case, the forefinger is able to be guided to a proper grip position by gripping the device (body) with the forefinger placed along the stepped portion. As a result, when the device (body) is gripped, the positions of the fingers are nearly fixed. For this reason, when the body is gripped with one hand, the finger of the one hand is able to be in reliable contact with the first electrocardiographic electrode.

In a handheld electrocardiographic measurement device according to a preferred embodiment of the present invention, a thickness of the flange is preferably larger in an edge portion than in an inner side portion.

In this case, since the flange is easily pinched, it is pinched without any excessive force (unnecessary force). For example, even when measurement is continued for a long period, the increase in myoelectric noise is significantly reduced or prevented.

A handheld electrocardiographic measurement device according to a preferred embodiment of the present invention preferably further includes an optical pulse wave sensor that acquires a pulse wave signal from a hand of the user.

In this case, a pulse wave signal is able to be simultaneously acquired in addition to the electrocardiographic signal. For this reason, when the heart rate is calculated from the electrocardiographic signal and the pulse rate is calculated from the pulse wave signal, the rates are able to be mutually complemented, and this increases the acquisition rate of biological information. Moreover, biological information, such as a pulse wave transit time, is also able to be acquired.

According to preferred embodiments of the present invention, handheld electrocardiographic measurement devices acquire an electrocardiographic signal from the fingers of both hands. Even when size reduction is performed, the fingers of both hands do not touch each other and rarely get tired even when holding the device for a long period. This allows the electrocardiographic signal to be stably measured for a long period.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
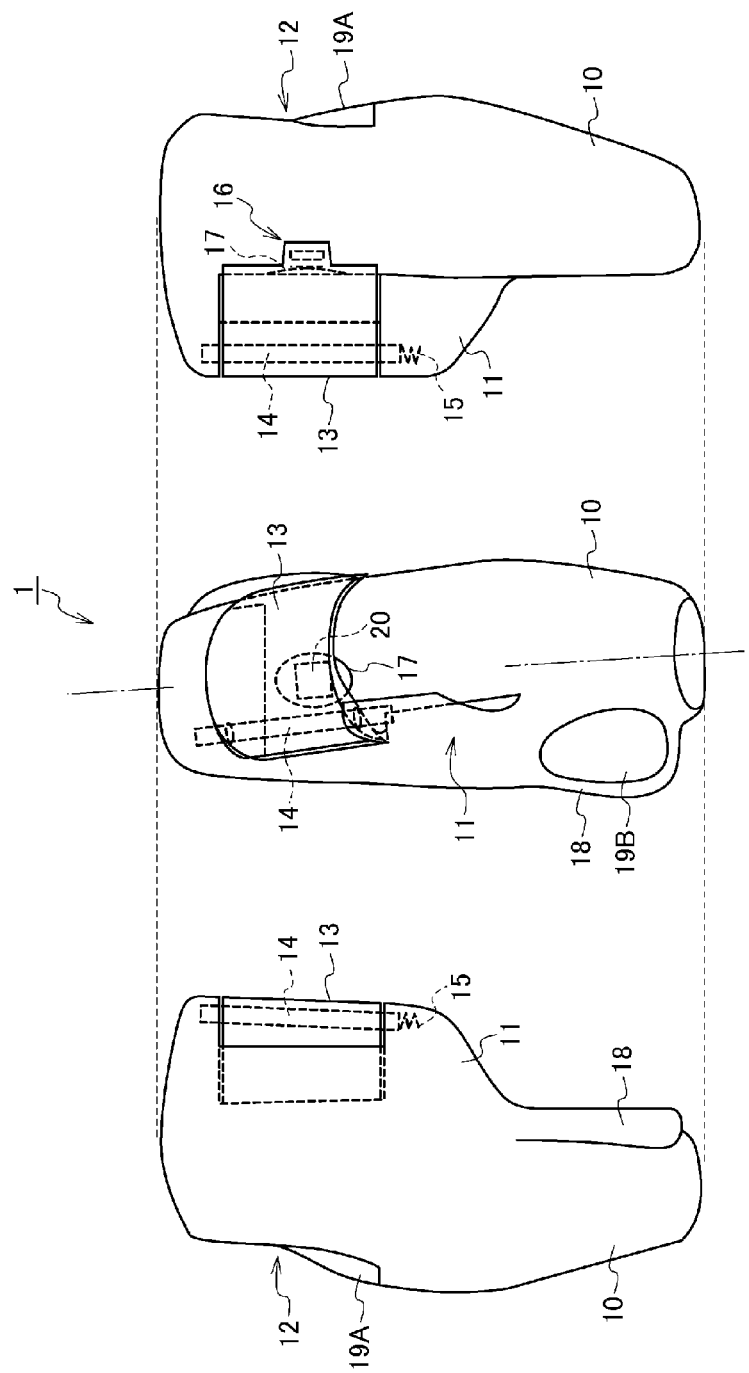
FIG. 1 includes a front view and left and right side views illustrating an outward appearance of a handheld electrocardiographic measurement device according to a first preferred embodiment of the present invention (in a state in which a shading cover is closed).
Figure 2:
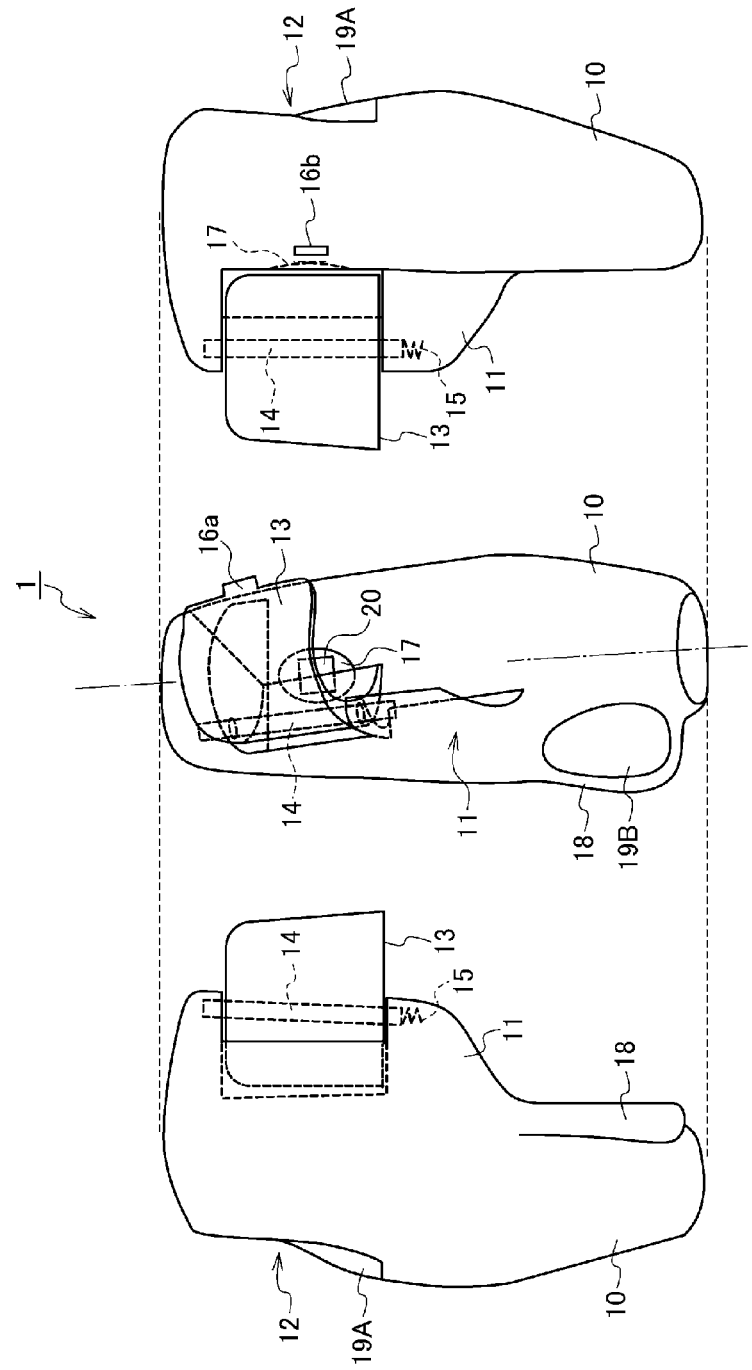
FIG. 2 includes a front view and left and right side views illustrating the outward appearance of the handheld electrocardiographic measurement device according to the first preferred embodiment of the present invention (in a state in which the shading cover is open).

Preferred embodiments of the present invention will be described in detail below with reference to the drawings. In the drawings, the same reference signs are used for the same or corresponding portions. In the drawings, the same or similar elements are denoted by the same signs, and overlapping descriptions thereof are omitted.

First Preferred Embodiment

Figure 3:
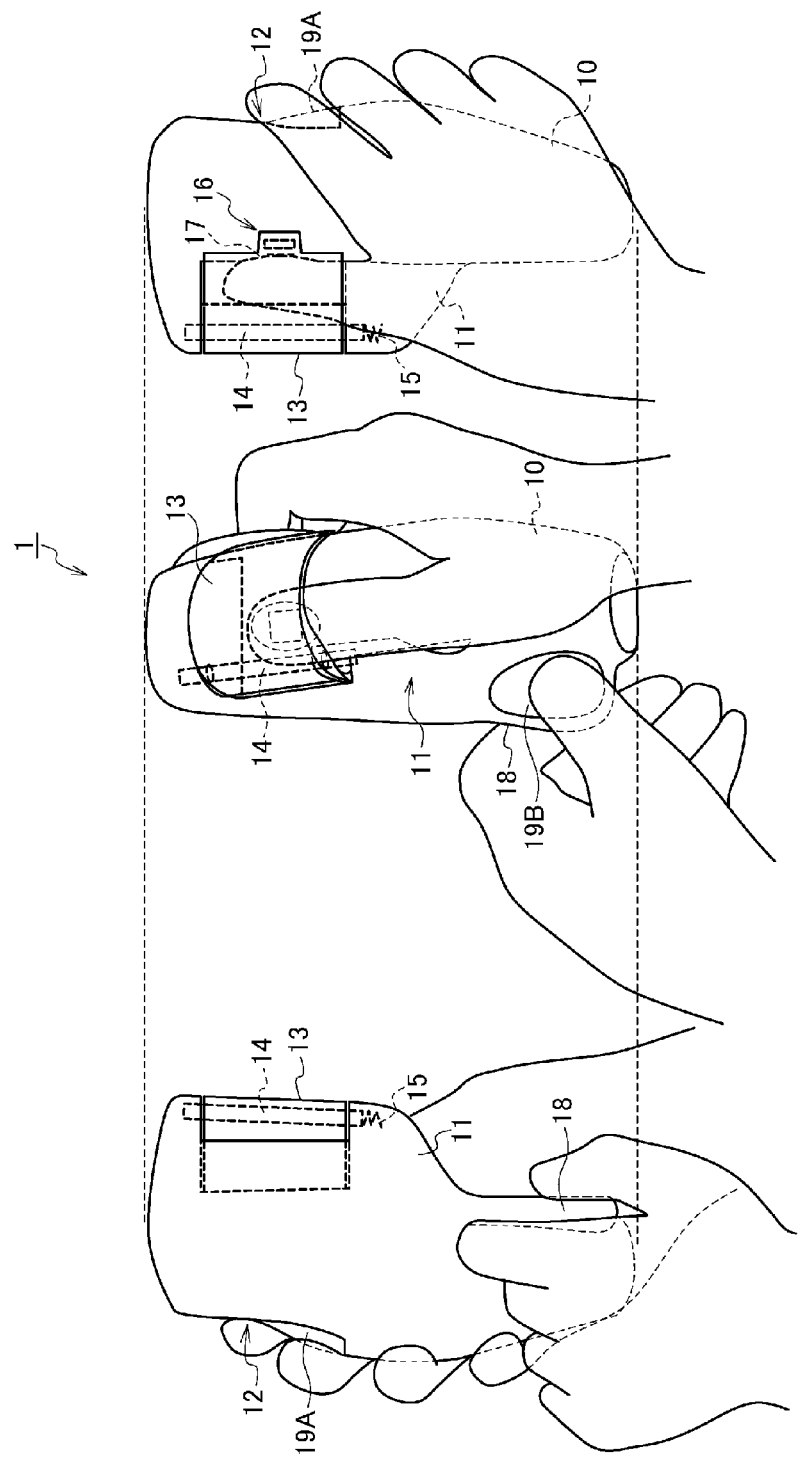
FIG. 3 illustrates a state in which the handheld electrocardiographic measurement device of the first preferred embodiment of the present invention is held with hands (in a measurement state).
Figure 4:
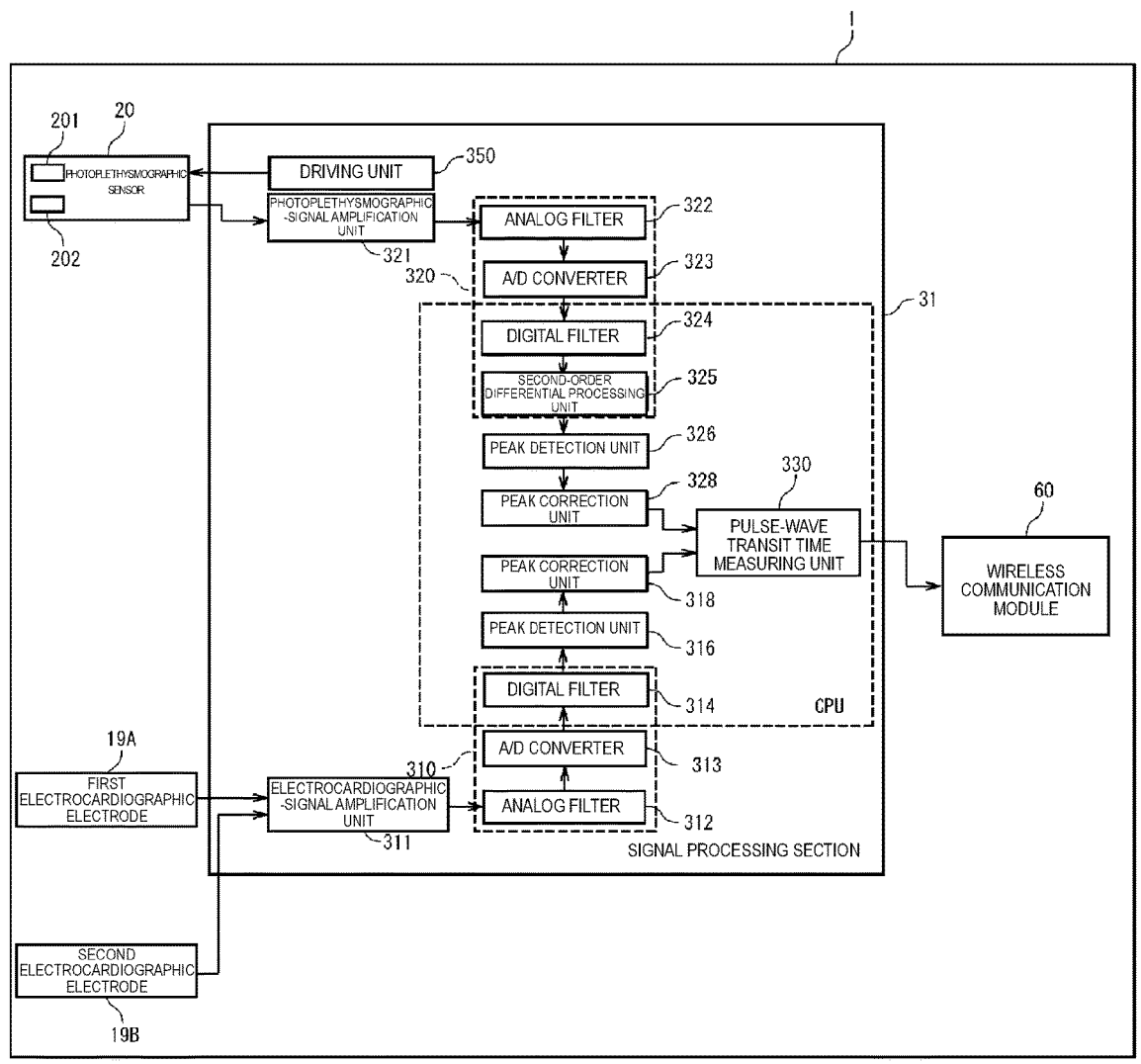
FIG. 4 is a block diagram showing a functional configuration of the handheld electrocardiographic measurement device according to the first preferred embodiment of the present invention.

First, a structure of a handheld electrocardiographic measurement device 1 according to a first preferred embodiment of the present invention will be described with reference to FIGS. 1 to 4 in combination. FIG. 1 includes a front view and left and right side views illustrating an outward appearance of the handheld electrocardiographic measurement device 1 of the first preferred embodiment (in a state in which a shading cover is closed), and FIG. 2 includes a front view and left and right side views illustrating the outward appearance of the handheld electrocardiographic measurement device 1 (in a state in which the shading cover is open). FIG. 3 illustrates a state in which the handheld electrocardiographic measurement device 1 is held with hands (a measurement state). FIG. 4 is a block diagram showing a functional configuration of the handheld electrocardiographic measurement device 1.

The handheld electrocardiographic measurement device 1 is a handheld electrocardiographic measurement device that is gripped by the user to acquire an electrocardiographic signal and a photoplethysmographic signals and to measure, for example, a heart rate, a pulse rate, and a pulse wave transit time.

The handheld electrocardiographic measurement device 1 includes a substantially spheroidal body 10 that the user grips with a thumb and the other four fingers of one hand (for example, the right hand) during measurement. In the body 10, a stopper (retaining portion) 11 projects along the axial direction of the body 10 (see a one-dot chain line in FIGS. 1 and 2) to restrict (stop) the position of the thumb of one hand of the user by abutting on side surfaces of a middle joint and a base joint of the thumb when the user grips the body 10 with the one hand. For example, the body 10 is preferably made of resin. Also, "substantially spheroidal" shape means that the shape is not limited to a spheroid geometrically defined in a strict sense.

At a position closer to a distal end portion than a center portion on the back side of the body 10 when viewed from the stopper 11, a stepped portion 12 (projection) is provided to guide the forefinger of one hand to a proper grip position when the body 10 (device 1) is gripped. That is, when the body 10 is gripped with the forefinger placed along the stepped portion 12, the positions of the fingers are fixed or substantially fixed, and this reduces variations in the vertical position of the tip of the thumb.

On a side surface of the body 10 (a side surface where the stopper 11 projects), a plate-shaped flange 18 projects in a direction orthogonal or substantially orthogonal to the projecting direction of the stopper 11 (that is, in a sideward direction). The flange 18 extends along the axial direction of the body 10 (that is, from a base end side toward a distal end side). Also, the thickness of the flange 18 is preferably larger in an outer edge portion (primarily on the back side) than in an inner side portion (center portion).

On the back side of the body 10, a first electrocardiographic electrode 19A is disposed at a position extending from the stepped portion 12 (projection) toward the base end side. That is, the first electrocardiographic electrode 19A is disposed so that the finger (for example, the forefinger and/or the middle finger) of one hand (for example, the right hand) comes into contact with the first electrocardiographic electrode 19A when the body 10 is gripped with the one hand.

On the other hand, on a surface of the flange 18 on the front side (and/or a surface on the back side), a second electrocardiographic electrode 19B preferably having, for example, an elliptical or substantially elliptical shape is disposed to detect an electrocardiographic signal. That is, the second electrocardiographic electrode 19B is disposed to come into contact with the finger (for example, the thumb and/or the forefinger) of the other hand (for example, the left hand) when the flange 18 is pinched (clamped) with the fingers (for example, the thumb and the forefinger) of the other hand.

That is, the first electrocardiographic electrode 19A and the second electrocardiographic electrode 19B acquire an electrocardiographic signal in accordance with the potential difference between the left and right hands of the user by coming into contact with the left and right hands (fingertips) of the user when the user grips the body 10 and the flange 18 of the handheld electrocardiographic measurement device 1. As the electrode materials of the first electrocardiographic electrode 19A and the second electrocardiographic electrode 19B, for example, a metal, such as a metal that is resistant to corrosion and causes little metal allergy, such as stainless steel or Au, a conductive gel, a conductive rubber, and a conductive cloth may preferably be used. As other electrode materials of the first electrocardiographic electrode 19A and the second electrocardiographic electrode 19B, for example, a conductive plastic material and a capacitive coupling electrode may be used. The first electrocardiographic electrode 19A and the second electrocardiographic electrode 19B are each connected through a cable to a signal processor 31 to be described later, and output the electrocardiographic signal to the signal processor 31 through the cable.

A shading cover (shading member) 13 having a shading function is attached to the body 10 to shield light so that disturbance light does not enter a photoplethysmographic sensor 20, which is to be described later, during measurement, and is opened and closed by swinging in the circumferential direction of the body 10. The shading cover 13 preferably has a semi-cylindrical or substantially semi-cylindrical shape (curved planar shape) to cover the user's thumb during measurement.

More specifically, the shading cover 13 is attached to the body 10 along the stopper 11 of the body 10 on the distal end side of the stopper 11 (body 10) to swing on a swing shaft 14 defined by a shaft parallel or substantially parallel to the axial direction of the body 10. In more detail, when viewed from the base end side of the body 10, the shading cover 13 is swing ably attached so that one end portion (edge) protrudes from the stopper 11 toward the photoplethysmographic sensor 20 when opened and the one end portion (edge) substantially matches an end surface of the stopper 11 when closed.

A bias member 15, such as a spring, for example, biasing the shading cover 13 in an opening direction is assembled in the swing shaft 14 of the shading cover 13. For this reason, the shading cover 13 is unlocked (details will be described later), and automatically opens when the user does not grip the body 10. The shading cover 13 swings close to cover the tip of the thumb along with the user's motion of moving the thumb into contact with the stopper 11 when gripping the body 10.

The shading cover 13 is provided with a lock mechanism 16 that locks (fixes) the shading cover 13 in a closed state, for example, when not used. More specifically, a claw portion 16a is provided in one end portion (edge) of the shading cover 13, and a groove portion 16b in which the claw portion 16a is to be fitted is provided in a side surface of the body 10. When the claw portion 16a provided in the end portion of the shading cover 13 is fitted in the groove portion 16b, the shading cover 13 is fixed (locked) to the body 10.

A photoplethysmographic sensor 20 is disposed at a position in the body 10 offset from the swing shaft 14 of the shading cover 13 in the circumferential direction of the body 10 (a position on the center line of the body 10). The photoplethysmographic sensor 20 includes a light emitting element 201 and a light receiving element 202, and acquires a photoplethysmographic signal from the tip of the thumb restricted by the stopper 11. The photoplethysmographic sensor 20 is a sensor that optically detects a photoplethysmographic signal by utilizing the light absorption characteristics of blood hemoglobin.

In the body 10, a region where the photoplethysmographic sensor 20 including the light emitting element 201 and the light receiving element 202 is disposed is preferably elliptical or substantially elliptical and is lower than a surrounding surface. That is, the photoplethysmographic sensor 20 is disposed in a central portion of a recess 17 provided in the body 10. For this reason, the user is able to reliably position the tip of the thumb on the photoplethysmographic sensor 20 without visual checking by putting the ball of the thumb in the recess 17.

As illustrated in FIG. 4, the light emitting element 201 emits light according to a pulsed driving signal output from a driver 350 of a signal processor 31 to be described later. As the light emitting element 201, for example, an LED, a VCSEL (Vertical Cavity Surface Emitting LASER), or a resonator LED can be used. The driver 350 generates and outputs a pulsed driving signal to drive the light emitting element 201.

The light receiving element 202 outputs a detection signal in accordance with the intensity of incident light emitted from the light emitting element 201 and passing through the thumb or reflected by the thumb. As the light receiving element 202, for example, a photodiode or a phototransistor may preferably be used. In this preferred embodiment, a photodiode is used as the light receiving element 202.

The light receiving element 202 is coupled to the signal processor 31, and a detection signal (photoplethysmographic signal) obtained by the light receiving element 202 is output to the signal processor 31.

The body 10 stores the signal processor 31 and a wireless communication module 60 that transmits measured biological information, such as an electrocardiographic signal, a photoplethysmographic signal, and a pulse wave transit time, to an external apparatus. The body 10 also stores a battery (not illustrated) which supplies power to, for example, the photoplethysmographic sensor 20, the signal processor 31, and the wireless communication module 60.

A pair of electrocardiographic electrodes (first electrocardiographic electrode 19A and second electrocardiographic electrode 19B) and the photoplethysmographic sensor 20 are coupled to the signal processor 31, and detected electrocardiographic and photoplethysmographic signals are input to the signal processor 31.

The signal processor 31 measures a pulse wave transit time from the time difference between the R-wave peak of the detected electrocardiographic signal (electrocardiographic wave) and the peak of the detected photoplethysmographic signal (pulse wave). The signal processor 31 also measures, for example, the heart rate and heartbeat interval by processing the input electrocardiographic signal. Further, the signal processor 31 measures, for example, the pulse rate and pulse interval by processing the input photoplethysmographic signal.

The signal processor 31 includes amplifiers 311 and 321, a first signal processor 310, a second signal processor 320, peak detectors 316 and 326, peak correctors 318 and 328, and a pulse-wave transit time calculator 330. The first signal processor 310 includes an analog filter 312, an A/D converter 313, and a digital filter 314. On the other hand, the second signal processor 320 includes an analog filter 322, an A/D converter 323, a digital filter 324, and a second-order differential processor 325.

Of the above-described elements, the digital filters 314 and 324, the second-order differential processor 325, the peak detectors 316 and 326, the peak correctors 318 and 328, and the pulse-wave transit time calculator 330 are defined by, for example, a CPU that performs arithmetic operations, a ROM that stores programs and data causing the CPU to perform the operations, and a RAM that temporarily stores various data, such as an operation result. That is, the functions of the elements are implemented by execution of the programs stored in the ROM by the CPU.

The amplifier 311 is preferably defined by, for example, an amplifier using an operational amplifier, and amplifies an electrocardiographic signal detected by the pair of electrocardiographic electrodes (first electrocardiographic electrode 19A and second electrocardiographic electrode 19B). The electrocardiographic signal amplified by the amplifier 311 is output to the first signal processor 310. Similarly, the amplifier 321 is preferably defined by, for example, an amplifier such as an operational amplifier, and amplifies a photoplethysmographic signal detected by the photoplethysmographic sensor 20. The photoplethysmographic signal amplified by the amplifier 321 is output to the second signal processor 320.

As described above, the first signal processor 310 includes the analog filter 312, the A/D converter 313, and the digital filter 314, and extracts a pulsation component by subjecting the electrocardiographic signal amplified by the amplifier 311 to filtering.

As described above, the second signal processor 320 includes the analog filter 322, the A/D converter 323, the digital filter 324, and the second-order differential processor 325, and extracts a pulsation component by subjecting the photoplethysmographic signal amplified by the amplifier 321 to filtering and second-order differential processing.

The analog filters 312 and 322 and the digital filters 314 and 324 perform filtering to remove components (noise) other than the frequencies characterizing the electrocardiographic signal and the photoplethysmographic signal to improve the S/N ratio. In more detail, in general, a frequency component of about 0.1 Hz to about 200 Hz is dominant in the electrocardiographic signal and a frequency component near 0.1 Hz to several tens of hertz is dominant in the photoplethysmographic signal. Thus, filtering is performed by using the analog filters 312 and 322 and the digital filters 314 and 324, such as a low pass filter and a bandpass filter, to selectively pass only signals in the above frequency ranges. This improves the S/N ratio.

When only extraction of the pulsation component is to be performed (that is, when there is no need to acquire, for example, the waveform), components other than the pulsation component may be cut by further narrowing the passing frequency range to improve noise immunity. The analog filters 312 and 322 and the digital filters 314 and 324 do not always need to both be provided, and either the analog filters 312 and 322 or the digital filters 314 and 324 may only be provided. The electrocardiographic signal filtered by the analog filter 312 and the digital filter 314 is output to the peak detector 316. Similarly, the photoplethysmographic signal filtered by the analog filter 322 and the digital filter 324 is output to the second-order differential processor 325.

The second-order differential processor 325 acquires a second-order differential pulse wave (acceleration pulse wave) signal by subjecting the photoplethysmographic signal to second-order differential. The acquired acceleration pulse wave signal is output to the peak detector 326. Since the peak (rising point) of the photoplethysmographic signal is sometimes difficult to detect because the change thereof is not clear, the photoplethysmographic signal is preferably converted into an acceleration pulse wave to enable peak detection. However, the second-order differential processor 325 is not essential, and may be omitted.

The peak detector 316 detects a peak (R-wave) of the electrocardiographic signal subjected to signal processing (the pulsation component is extracted) by the first signal processor 310. On the other hand, the peak detector 326 detects a peak of the photoplethysmographic signal (acceleration pulse wave) filtered by the second signal processor 320. The peak detector 316 and the peak detector 326 each detect the peak within normal ranges of the heartbeat interval and pulse interval, and, for example, store information about the peak time and the peak amplitude of all detected peaks in the RAM.

The peak corrector 318 determines a delay time of the electrocardiographic signal in the first signal processor 310 (analog filter 312 and digital filter 314). The peak corrector 318 corrects the peak of the electrocardiographic signal detected by the peak detector 316 based on the delay time of the electrocardiographic signal. Similarly, the peak corrector 328 determines a delay time of the photoplethysmographic signal in the second signal processor 320 (analog filter 322, digital filter 324, and second-order differential processor 325). The peak corrector 328 corrects the peak of the photoplethysmographic signal (acceleration pulse wave signal) detected by the peak detector 326 based on the delay time of the photoplethysmographic signal. The corrected peak of the electrocardiographic signal and the corrected peak of the photoplethysmographic signal (acceleration pulse wave) are output to the pulse-wave transit time calculator 330. The peak corrector 318 is not essential, and may be omitted.

The pulse-wave transit time calculator 330 determines a pulse wave transit time from the interval (time difference) between the R-wave peak of the electrocardiographic signal corrected by the peak corrector 318 and the peak of the photoplethysmographic signal (acceleration pulse wave) corrected by the peak corrector 328.

In addition to the pulse wave transit time, the pulse-wave transit time calculator 330 calculates, for example, the heart rate, the heartbeat interval, and the heartbeat interval change rate from the electrocardiographic signal. Similarly, the pulse-wave transit time calculator 330 calculates, for example, the pulse rate, the pulse interval, and the pulse-interval change rate from the photoplethysmographic signal (acceleration pulse wave).

The acquired measurement data, such as the pulse wave transit time, the heart rate, and the pulse rate, are transmitted through the wireless communication module 60 to, for example, a PC, a mobile music player having a display, or a smartphone. In this case, data regarding, for example, the measurement date, is preferably transmitted in addition to the measurement result and the detection result.

Next, a description will be provided of a method of using the handheld electrocardiographic measurement device 1. When detecting an electrocardiographic signal and a photoplethysmographic signal and measuring, for example, the heart rate, the pulse rate, and the pulse wave transit time with the handheld electrocardiographic measurement device 1, as illustrated in FIG. 3, the body 10 of the handheld electrocardiographic measurement device 1 is gripped with the thumb and the other four fingers of one hand (for example, the right hand). Thus, the finger (for example, the forefinger and/or the middle finger) of the one hand come into contact with the first electrocardiographic electrode 19A.

At this time, as described above, when the shading cover 13 is unlocked and the user does not grip the body 10, the shading cover 13 automatically opens. Thus, the user is able to naturally grip the body 10. When the user grips the body 10 with one hand and moves the thumb of the one hand into contact with the stopper (from the right side to the left side in the example of FIG. 3), an end portion (edge) of the shading cover 13 is pressed by the thumb, and the shading cover 13 swings and closes to cover the tip of the thumb. Then, the tip of the thumb is brought into contact with the photoplethysmographic sensor 20 by putting the ball of the thumb in the recess 17.

On the other hand, the flange 18 is pinched (clamped) with the thumb and the forefinger of the other hand (for example, the left hand). Thus, the finger of the other hand (the thumb and/or the forefinger) comes into contact with the second electrocardiographic electrode 19B.

In this case, an electrocardiographic signal is acquired by the pair of electrocardiographic electrodes (first electrocardiographic electrode 19A and second electrocardiographic electrode 19B), and at the same time, a photoplethysmographic signal is acquired by the photoplethysmographic sensor 20. Then, a pulse wave transit time is acquired by the signal processor 31 from the peak time difference between the electrocardiographic signal and the photoplethysmographic signal. Since the method for acquiring, for example, the pulse wave transit time has been described above, a detailed description thereof is omitted here.

In this manner, the user is able to detect and measure, for example, the electrocardiographic signal, the photoplethysmographic signal, and the pulse wave transit time only by holding the handheld electrocardiographic measurement device 1 with both hands. The detected and measured biological information, such as the electrocardiographic signal, the photoplethysmographic signal, and the pulse wave transit time, is transmitted to the external apparatus by the wireless communication module 60.

As described in detail above, according to the present preferred embodiment, when the device 1 is held with both hands, the substantially spheroidal body 10 is gripped with one hand (the thumb and the other four fingers), and the plate-shaped flange 18 is pinched (clamped) with the fingers (for example, the thumb and the forefinger) of the other hand. Since both hands support each other, they rarely get tired even when maintaining their posture for a long period (for example, several minutes). At this time, since the body 10 is gripped in such a manner that the finger of one hand (for example, the forefinger and/or the middle finger) touches the first electrocardiographic electrode 19A disposed on the back side of the body 10 and the finger of the other hand (for example, the thumb and/or the forefinger) touches the second electrocardiographic electrode 19B disposed on the surface of the flange 18, the fingers of both hands are placed close to each other. However, the position of the thumb of the one hand is restricted by the stopper 11 projecting along the axial direction of the body 10, and the plate-shaped flange 18 projects from the side surface of the body 10 in the direction orthogonal or substantially orthogonal to the projecting direction of the stopper 11. This prevents the contact between the fingers of both hands. That is, both hands are able to hold the device 1 without touching each other. As a result, even if the size is reduced, the fingers of both hands do not touch each other and rarely become tired even when holding the device 1 for a long period. This allows the electrocardiographic signal to be stably measured for a long period.

According to the present preferred embodiment, the stepped portion 12 is provided at the position on the back side of the body 10 near the distal end portion. For this reason, when the device 1 (body 10) is gripped, the forefinger is guided to the proper grip position by gripping the device 1 with the forefinger placed along the stepped portion. As a result, when the device 1 (body 10) is gripped, the positions of the fingers are fixed or substantially fixed. For this reason, when the body is gripped with one hand, the finger of the one hand is able to be reliably brought into contact with the first electrocardiographic electrode 19A.

According to the present preferred embodiment, the thickness of the flange 18 is preferably larger in the outer edge portion than in the inner side portion (center portion). As a result, the flange is easily pinched. Thus, the flange 18 is pinched without any excessive force (unnecessary force). For example, even when measurement is continued for a long period, the increase in myoelectric noise is reduced or prevented.

According to the present preferred embodiment, the photoplethysmographic signal is able to be simultaneously acquired, in addition to the electrocardiographic signal. For this reason, for example, when the heart rate is calculated from the electrocardiographic signal and the pulse rate is calculated from the photoplethysmographic signal, the rates are able to be mutually complemented, and this increases the acquisition rate of biological information. Moreover, biological information, such as the pulse wave transit time, is able to be acquired.

Further, according to the present preferred embodiment, when the body 10 is gripped with one hand and the thumb is moved onto the photoplethysmographic sensor 20, the stopper 11 allows the thumb to be easily positioned on the photoplethysmographic sensor 20. At this time, since the shading cover 13 is swung and closed by being pressed by the thumb, the thumb is covered with the shading cover 13 and entry of disturbance light is prevented. This allows stable measurement.

According to the present preferred embodiment, since the shading cover 13 includes the bias member 15 biasing the shading cover 13 in the opening direction, it automatically opens when the device 1 (body 10) is not gripped. For this reason, when the device 1 is gripped, the shading cover 13 does not interfere with the gripping. Thus, the device 1 (body 10) is able to be naturally gripped without forcing any unnatural operation.

According to the present preferred embodiment, since the shading cover 13 is attached to swing on the swing shaft 14 extending parallel or substantially parallel to the axial direction of the body 10, the shading cover 13 is able to be swung and closed to cover the tip of the thumb by a series of natural operations of gripping the device 1 (body 10), sliding the thumb in the lateral direction, and moving the thumb onto the photoplethysmographic sensor 20.

According to the present preferred embodiment, since the lock mechanism 16 is provided to lock (fix) the shading cover 13 in a closed state, when the device 1 is not used, the shading cover 13 is fixed in the closed state. Thus, for example, it is possible to reduce the risk of damage when the device 1 is transported or dropped.

Second Preferred Embodiment

While the first electrocardiographic electrode 19A preferably is disposed on the back side of the body 10 in the handheld electrocardiographic measurement device 1 of the first preferred embodiment, a first electrocardiographic electrode 19C may preferably be disposed in the recess 17.

Figure 5:
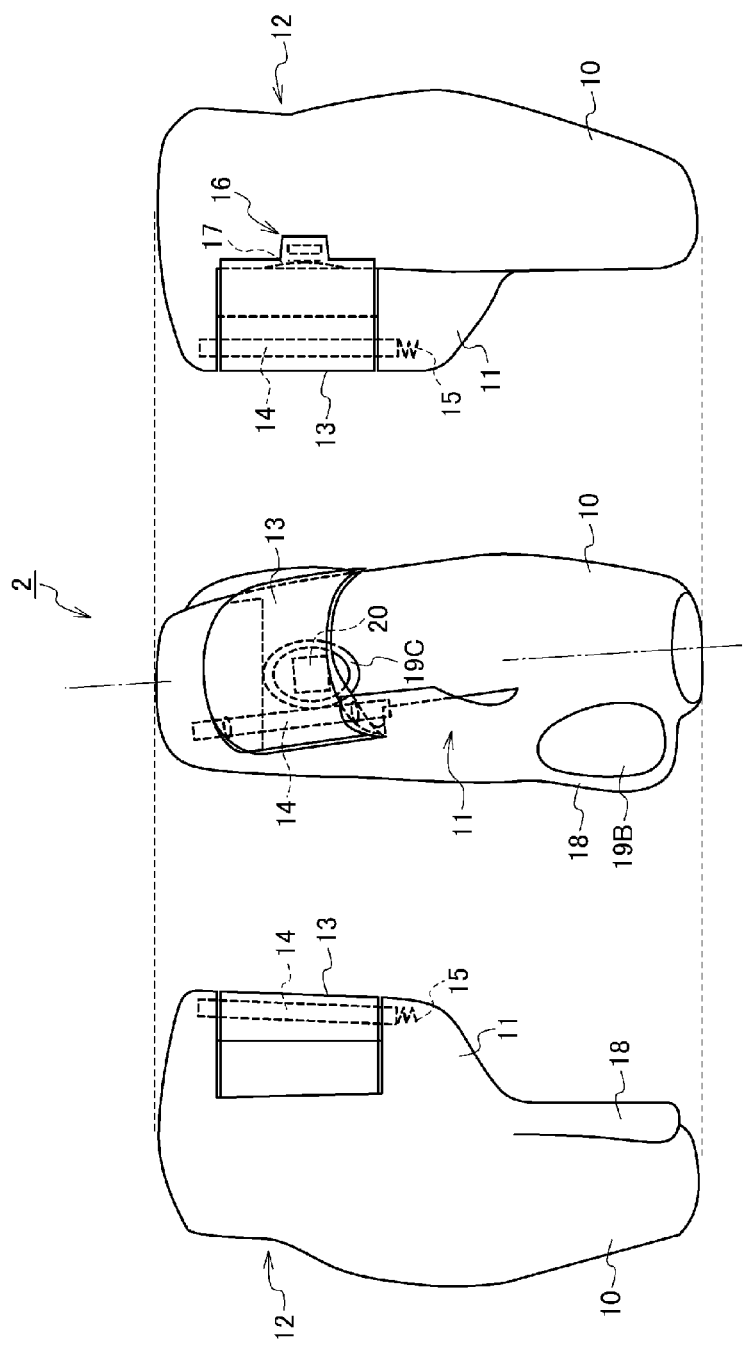
FIG. 5 includes a front view and left and right side views illustrating an outward appearance of a handheld electrocardiographic measurement device according to a second preferred embodiment of the present invention (in a state in which a shading cover is closed).

Accordingly, a handheld electrocardiographic measurement device 2 according to a second preferred embodiment of the present invention will be next described with reference to FIG. 5. Herein, descriptions of the same and similar structures to those of the first preferred embodiment are simplified or omitted, and differences are primarily described. FIG. 5 includes a front view and left and right side views illustrating an outward appearance of the handheld electrocardiographic measurement device 2 of the second preferred embodiment (in a state in which a shading cover is closed). In FIG. 5, the same or equivalent structural elements to those of the first preferred embodiment are denoted by the same signs.

The handheld electrocardiographic measurement device 2 is different from the handheld electrocardiographic measurement device 1 of the first preferred embodiment in that a ring-shaped first electrocardiographic electrode 19C is disposed along an outer edge of a recess 17 provided around a photoplethysmographic sensor 20, and preferably, so as to surround the photoplethysmographic sensor 20. That is, the first electrocardiographic electrode 19C is disposed at a position offset from a stopper 11 (a swing shaft 14 of a shading cover 13) in the circumferential direction of a body 10. When the body 10 is gripped with one hand (for example, the right hand), the tip (ball) of the thumb of the one hand restricted by the stopper 11 touches the first electrocardiographic electrode 19C.

Since other structures are the same as or similar to those of the above-described handheld electrocardiographic measurement device 1, detailed descriptions thereof are omitted herein. The first electrocardiographic electrode 19C may be disposed in an inner side portion of the recess 17 (that is, around the photoplethysmographic sensor 20).

According to the present preferred embodiment, when the device is held with both hands, one hand (the thumb and the other four fingers) grips the substantially spheroidal body 10 and the fingers of the other hand (for example, the thumb and the forefinger) pinch (clamp) a plate-shaped flange 18. Since both hands support each other, they rarely become tired even when maintaining their posture for a long period (for example, several minutes). Further, at this time, while the thumb of one hand touches the first electrocardiographic electrode 19C disposed in the body and the finger of the other hand (the thumb and/or the forefinger) touches a second electrocardiographic electrode 19B disposed on the surface of the flange 18, the position of the thumb of the one hand is restricted by the stopper 11 projecting along the axial direction of the body 10. Moreover, the plate-shaped flange 18 projects from the side surface of the body 10 in the direction orthogonal or substantially orthogonal to the projecting direction of the stopper 11. Thus, the fingers of both hands are prevented from touching each other. That is, the device 2 is able to be held with both hands while the hands do not touch each other. As a result, even when the size is reduced, the fingers of both hands do not touch each other and rarely become tired even when holding the device for a long period. This allows an electrocardiographic signal to be stably measured for a long period. Particularly in this case, since the pair of electrocardiographic electrodes 19B and 19C are disposed on the same side (front side), it is possible to easily and visually check whether or not the fingers of both hands respectively touch the pair of electrocardiographic electrodes 19B and 19C.

According to the present preferred embodiment, since a region of the body 10 in which the first electrocardiographic electrode 19C is disposed is lower than a surrounding surface, the tip of the thumb is able to be reliably brought into contact with the first electrocardiographic electrode 19C by putting the ball of the thumb in the recess 17.

While the preferred embodiments of the present invention have been described above, the present invention is not limited to the above-described preferred embodiments, and various modifications can be made. For example, the shape of the handheld electrocardiographic measurement devices 1 and 2 may be different between the right-handed user and the left-handed user so that the stopper 11 and the flange 18 are symmetrical or substantially symmetrical in the right-left direction.

While the handheld electrocardiographic measurement devices 1 and 2 each include the photoplethysmographic sensor 20 in the above-described preferred embodiments, for example, the photoplethysmographic sensor 20 may be replaced with a piezoelectric pulse wave sensor or an oxygen saturation sensor. The photoplethysmographic sensor 20 and the shading cover 13 are not essential, and may be omitted.

While detected and measured information (measurement data), such as the photoplethysmographic signal and the pulse rate, is transmitted to the external apparatus by the wireless communication module 60 in the above-described preferred embodiments, acquired information (measurement data) may be stored in a memory inside the device during measurement and the data may be transferred while the device is connected to the external apparatus after measurement is completed.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A handheld electrocardiographic measurement device comprising:
    a substantially spheroidal body;
    a stopper projecting along an axial direction of the body to restrict a position of a thumb of one hand by abutting on a side surface of the thumb when a user grips the body with the one hand;
    a plate-shaped flange projecting from a side surface of the body in a direction orthogonal or substantially orthogonal to a projecting direction of the stopper;
    a first electrocardiographic electrode disposed on a back side of the body to contact a finger of the one hand when the body is gripped with the one hand; and
    a second electrocardiographic electrode disposed on a surface of the flange to contact a finger of the other hand when the flange is pinched by the other hand; wherein
    a portion of the stopper is disposed between the first electrocardiographic electrode and the second electrocardiographic electrode.

2. The handheld electrocardiographic measurement device according to claim 1, wherein a stepped portion is provided at a position near a distal end portion of the body on the back side, when viewed from the stopper.

3. The handheld electrocardiographic measurement device according to claim 1, wherein a thickness of the flange is larger in an edge portion than in an inner side portion.

4. The handheld electrocardiographic measurement device according to claim 1, further comprising:
    an optical pulse wave sensor configured to acquire a pulse wave signal from a hand of the user.

5. The handheld electrocardiographic measurement device according to claim 4, further comprising a shading cover attached to the body and structured to provide shade to the optical pulse wave sensor.

6. The handheld electrocardiographic measurement device according to claim 5, wherein the shading cover has a semi-cylindrical or substantially semi-cylindrical shape.

7. The handheld electrocardiographic measurement device according to claim 5, wherein the shading cover is attached to the body along the stopper on a distal end side of the stopper, and structured to swing on a swing shaft extending parallel or substantially parallel to the axial direction of the body.

8. The handheld electrocardiographic measurement device according to claim 7, wherein a bias member biasing the shading cover in an opening direction is provided in the swing shaft.

9. The handheld electrocardiographic measurement device according to claim 5, wherein the shading cover includes a lock mechanism that locks the shading cover in a closed state.

10. A handheld electrocardiographic measurement device comprising:
    a substantially spheroidal body;
    a stopper projecting along an axial direction of the body to restrict a position of a thumb of one hand by abutting on a side surface of the thumb when a user grips the body with the one hand;
    a plate-shaped flange projecting from a side surface of the body in a direction orthogonal or substantially orthogonal to a projecting direction of the stopper;
    a first electrocardiographic electrode disposed at a position offset from the stopper along a circumferential direction of the body to contact the thumb restricted by the stopper when the body is gripped with the one hand; and
    a second electrocardiographic electrode disposed on a surface of the flange to contact a finger of the other hand when the flange is pinched by the other hand; wherein
    a portion of the stopper is disposed between the first electrocardiographic electrode and the second electrocardiographic electrode.

11. The handheld electrocardiographic measurement device according to claim 10, wherein a region of the body where the first electrocardiographic electrode is disposed is lower than a surrounding surface.

12. The handheld electrocardiographic measurement device according to claim 10, wherein a stepped portion is provided at a position near a distal end portion of the body on the back side, when viewed from the stopper.

13. The handheld electrocardiographic measurement device according to claim 10, wherein a thickness of the flange is larger in an edge portion than in an inner side portion.

14. The handheld electrocardiographic measurement device according to claim 10, further comprising:

an optical pulse wave sensor configured to acquire a pulse wave signal from a hand of the user.

15. The handheld electrocardiographic measurement device according to claim 14, wherein the first electrocardiographic electrode is provided around the optical pulse wave sensor.

16. The handheld electrocardiographic measurement device according to claim 14, further comprising a shading cover attached to the body and structured to provide shade to the optical pulse wave sensor.

17. The handheld electrocardiographic measurement device according to claim 16, wherein the shading cover has a semi-cylindrical or substantially semi-cylindrical shape.

18. The handheld electrocardiographic measurement device according to claim 16, wherein the shading cover is attached to the body along the stopper on a distal end side of the stopper, and structured to swing on a swing shaft extending parallel or substantially parallel to the axial direction of the body.

19. The handheld electrocardiographic measurement device according to claim 18, wherein a bias member biasing the shading cover in an opening direction is provided in the swing shaft.

20. The handheld electrocardiographic measurement device according to claim 16, wherein the shading cover includes a lock mechanism that locks the shading cover in a closed state.

\* \* \* \* \*